(12) United States Patent
Sperling et al.

(10) Patent No.: US 7,006,229 B2
(45) Date of Patent: Feb. 28, 2006

(54) MEANS FOR ILLUMINATING A MEASUREMENT SURFACE AND DEVICE AND METHOD FOR DETERMINING THE VISUAL PROPERTIES OF OBJECTS

(75) Inventors: Uwe Sperling, Geretsried (DE); Peter Schwarz, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 150 days.

(21) Appl. No.: 10/267,578

(22) Filed: Oct. 9, 2002

(65) Prior Publication Data

US 2003/0151746 A1 Aug. 14, 2003

(30) Foreign Application Priority Data

Oct. 9, 2001 (DE) ................................ 101 49 780

(51) Int. Cl.
*G01N 21/55* (2006.01)
(52) U.S. Cl. ...................................... 356/445; 356/600
(58) Field of Classification Search ........ 356/600–601, 356/445–446, 237.2, 237.3, 237.4, 237.5, 356/317–318, 417; 250/559.16, 559.19, 250/559.45; 362/545
See application file for complete search history.

(56) References Cited

U.S. PATENT DOCUMENTS

| | | | | |
|---|---|---|---|---|
| 4,945,228 A | * | 7/1990 | Juvinall et al. | 250/223 B |
| 5,406,060 A | * | 4/1995 | Gitin | 235/462.42 |
| 5,757,528 A | * | 5/1998 | Bradley et al. | 398/129 |
| 5,839,186 A | * | 11/1998 | Onodera | 29/720 |
| 6,177,954 B1 | * | 1/2001 | Bouvier | 348/92 |

* cited by examiner

*Primary Examiner*—Layla G. Lauchman
(74) *Attorney, Agent, or Firm*—Greer, Burns & Crain, LTD

(57) ABSTRACT

Illuminating means for illuminating a measurement surface and device for determining the properties of reflective objects. The illuminating means comprises a radiating means having radiation sources, an aperture means and a scattering means. The scattering means is arranged in the path of radiation and the light emitted by the sources of radiation is directable to the aperture means. The device comprises an illuminating means as a first optical means which radiates light onto a measurement surface. Said first optical means has a radiating means comprising radiation sources, an aperture means and a scattering means arranged in the path of radiation. The light emitted by the sources of radiation is directable to the aperture means. A second optical means is configured as detector means and registers the light reflected from the measurement surface. Said detector means outputs a measurement value which is characteristic for at least a portion of the light as received. A memory means is furthermore provided and a control means serves for the controlling of the measurement sequence, wherein a characteristic parameter which characterizes the measurement surface is determined.

47 Claims, 6 Drawing Sheets

Figure 1:
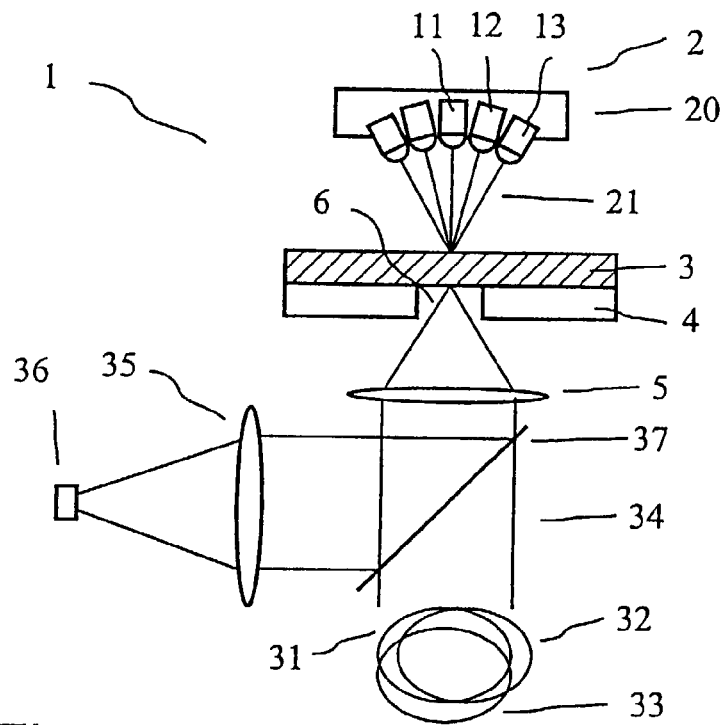

MEANS FOR ILLUMINATING A MEASUREMENT SURFACE AND DEVICE AND METHOD FOR DETERMINING THE VISUAL PROPERTIES OF OBJECTS

The present invention relates to a means for illuminating a measurement surface as well as a device and a method for determining the visual properties of objects.

For a great number of products—automobiles, for example—the visual properties of an object, respectively of a surface, constitute an important feature as far as the product's overall appearance. In order to achieve a high reproducibility during manufacturing or in the repairing of objects, measurements are thus made on prototypes or products for purposes of quality control in which one or several characteristic parameters are determined.

In so doing, a surface or object to be measured is illuminated by an illuminating means and a portion of the reflected (or also transmitted) light is received by one or more measuring means for the purpose of determining the visual properties of the measured object. The illuminating means used to illuminate the surface or object to be measured is an important component of the measuring device.

It is thus the task of the present invention to provide a means for illuminating a surface and a device and a method for determining the visual properties of objects of the type as indicated above.

Preferred embodiments of the invention constitute the subject matter of the subclaims.

A means according to the present invention for illuminating a measurement surface comprises at least one illuminating means which has at least two sources of radiation and at least one aperture means for limiting the aperture. At least one control means is arranged in the path of radiation.

Preferably, the light emitted by the radiation sources can be directed to the aperture means.

The light emitted by the radiation sources is preferably directed substantially in a common direction. This can mean, for example, that the axes through the main directions of propagation are aligned parallel to one another, or intersect at an oblique angle, or intersect at an oblique angle in a projection plane perpendicular to the measurement surface.

The inventive illuminating means has numerous advantages.

In a preferred embodiment of the present invention, a plurality of radiation sources is provided in at least one illuminating means, whereby the number of radiation sources amounts to =3 in at least one illuminating means. The number of these sources of radiation is preferably greater than 8, 12 or =16. In like manner, more than 16 or, for example, 18, 20, 24 or any such arbitrary number of radiation sources can be provided.

In another preferred embodiment of the present invention, at least two sources of radiation comprise at least one illuminating means exhibiting differing spectral characteristics.

It is preferable to provide a plurality of radiation sources having differing spectral characteristics.

It is especially preferable for the spectral characteristics of the different radiation sources to at least partially overlap. It is nevertheless possible in all cases for two or more differing sources of radiation to exhibit the same or substantially the same spectral characteristics so as to, for example, increase intensity in the corresponding spectral range.

In an embodiment of the present inventive device, at least one illuminating means emits radiation which substantially covers the entire visible range of the spectrum. This is of advantage in assessing visual properties across the entire visible range of the spectrum. Same can also be achieved by a plurality of radiation sources emitting spectrally-different light. Radiation can also be emitted in the UV and the infrared range.

Preferably, at least one radiation source of at least one illuminating means is a thermal emitter or a semiconductor source of illumination. Especially preferred is the realizing of at least one (or substantially all) source(s) of radiation as light-emitting diodes.

Semiconductor sources of radiation and light-emitting diodes and the like have numerous and particular advantages. For example, semiconductor sources of radiation have quick response times and need only comparatively little time to stabilize the radiated output. Other advantages of semiconductor illumination sources include long life and relatively low wear, etc.

Typical light-emitting diodes usually only radiate output across a relatively small range of wavelength. The entire visible spectrum (and even more) can be covered with the corresponding number of spectrally-differing radiating light sources. It is also possible to use white light LEDs.

At least one controlling means is preferably provided to control the illuminating means. The controlling means can hereto be configured such that it is possible for at least two sources of radiation of at least one illuminating means to emit light successively.

The illuminating means can be preferably regulated by the controlling means such that at least two sources of radiation will emit light substantially simultaneously.

It is particularly preferential to provide for both control variants so that, for example, depending on the user's need, or within the confines of a given illumination sequence, single or all sources of radiation will emit light successively and/or, at least at times, simultaneously.

When light is emitted simultaneously for at least a certain period of time, illumination ensues at a greater wavelength interval and/or at greater intensity, which can be of advantage.

When two or more radiation sources of one or more illuminating means are activated successively over a period of time, the measurement surface will be illuminated by a spectrum which varies over time, especially given spectrally-different emission characteristics. One advantage of such a procedure, for example, is that it allows conclusions to be drawn about the spectral properties of a surface even when utilizing only just a brightness sensor.

In a preferred embodiment of the inventive device in accordance with one or all of the previously described embodiments, at least one light guiding means is provided in the path of radiation between at least one radiation source of at least one illuminating means and the measurement surface to be illuminated. Said light guiding means is preferably provided in the path of radiation between the source of radiation and the aperture means in order to direct at least a portion of the light emitted by the source of radiation to said aperture means.

Such a measure allows for increasing the intensity of the emitted light behind the aperture means so that the relative influence of ambient diffused light decreases and a better signal-to-noise ratio is yielded.

Preferably, at least one light guiding means comprises at least one light guiding element. Said light guiding means preferably directs the light of different radiation sources to the aperture means. A separate or a common light guiding element can hereby be provided on the light guiding means for each individual source of radiation respectively.

Lenses and micro-lens elements or also micro-lens arrays are preferred as light guiding elements. Likewise preferred is utilizing diffraction elements as light guiding elements such as, for example, grid elements. Especially preferred in the case of diffraction elements is the use of volume grid elements or holographic-optical elements. Holographic-optical elements offer the advantage of flexible optical geometry and a flexible wavelength selection. With volume holograms as holographic-optical elements, the desired geometry and working wavelength can be readily adjusted by the volume hologram layer thickness, exposure wavelength and geometry.

Such elements enable radiation striking the holographic-optical element from a first direction to be directed to the aperture means exactly as is the radiation coming from a second direction. Controlling of the ray's path can transpire in a wavelength-selective manner so that light of a first wavelength range coming from a first direction is diverted while the light of a second wavelength range from the same first direction passes through unimpeded or is diverted to a second direction. The corresponding mutual dependence of wavelength and diffraction angle responds to the Bragg vector.

Utilizing the relevant holographic or non-holographic optical elements enables a flexible construction to the inventive illuminating means, whereby the corresponding light guiding means can divert the light emitted from a plurality of radiation sources to the aperture means.

In a preferred embodiment of the present invention, at least two and preferably at least 3, 4, 5, 6 or more radiation sources are arranged on a common carrier means and hereto preferably such that the respectively emitted radiation is at least partially or substantially directed to the aperture means.

The individual sources of radiation of an illuminating means may be arranged directly adjacent one another on the carrier means, whereby the spacing may be less than 5 mm or even less than 1 mm.

Said carrier means can hereby be, for example, a flat substrate of, for example, round, square or also other form. The individual sources of radiation (e.g. light-emitting diodes) may be arranged parallel to one another on the carrier means. The light emitted by said individual radiation sources will then be emitted substantially parallelly. Hereby, a central region of the radiation sources directly over the iris will emit to same at greater intensity than radiation sources which are arranged at a greater distance from the central optical axis.

The carrier means may likewise be configured three-dimensionally and in fact such that each individual source of radiation disposed on the carrier means is at least substantially directed or focused onto the aperture means. This allows for increasing of the emitted radiation as output to said aperture means.

The carrier means may also be provided with a light-conducting means such as, for example, the light guiding means as already described above so as to direct the light emitted by the individual sources of radiation to the preferable (e.g. centrally arranged) aperture means. Hereby, the use of reflecting elements is also possible for diverting the light striking each respective reflecting element to the aperture means.

To obtain a high reproducibility to the emitted radiation with different illuminating means, the carrier means is preferably configured such that the individual radiating elements are supported in a substantially fixed—but preferably inter-changeable—manner on said carrier means. A form-fit keeps adjustments to a minimum.

A preferred embodiment of the present invention provides for the individual light-emitting elements to be configured as semiconductor emitter elements and having substantially no housing and/or glass or plastic bodies in their guiding of light. These may be silicon chips.

It is then possible to affix a plurality of identical or differing illuminating elements on a proportionately small surface area of a carrier means. The carrier means can be made of ceramic or another non-conductive material with the individual illuminating elements being glued or affixed to said carrier means. This type of construction enables up to 10, 20, 30 or even more illuminating elements to be provided on a surface area of about 1 cm$^2$, for example.

The radiation emitted by the individual sources of radiation, the light sources or silicon chips respectively, may, given certain circumstances, be less directional as is the case with conventional light-emitting diodes. Although due to the high packing density, a large number of radiation sources can be disposed at close range to one another and to the aperture means so that a relatively high intensity of illumination will also be yielded.

A light guiding system can additionally be provided in the exact configuration as described above which, for example, also comprises conventional optical or also holographic-optical elements. Given such measures, the intensity of radiation to the aperture means can be increased even given a low volume output. Light guiding elements can divert or focus the radiation of individual or of all light sources onto the aperture means.

In a preferred embodiment of the present invention, at least one illuminating means is arranged to be movable. Preferably, the carrier means with said illuminating means or radiation source arranged thereon is likewise arranged to be moveable.

It is then preferable for the radiation sources on the carrier means to be arranged such that the respectively emitted light is directable to the aperture means. This can transpire, for example, by moving the carrier means relative the aperture means. The construction can hereby be such that substantially only the radiation of one respective light source will be emitted to the aperture means.

Moving the carrier means preferably ensues using a motor device with a stepper motor device being particularly preferred. An automatic positioning of the carrier means/respective radiation sources relative the aperture means is preferred so that individual sources of radiation can emit light toward said aperture means in successive fashion. Configured as such, a relatively high intensity of illumination can be radiated to the aperture means in respectively highly specific fashion.

It is especially preferred for the carrier means to be rotatable through at least one range of angles. The carrier means may be continuously rotatable or also rotatable only over a certain specific angular range.

In both respective cases, sliding contacts can be provided to generate an electrical connection from, e.g. an axis of rotation of the carrier means to the illumination elements arranged thereupon.

A switching means can furthermore be arranged on the carrier means for controlling the individual sources of radiation and/or stabilization of the electrical power supply for the radiation sources. The individual radiation sources of the carrier means can likewise be connected to other elements of the illuminating means by conventional electrical cable, especially when the carrier means can only be rotated through a specific angular range or only moved across a certain section of distance.

A rotatable carrier means is especially advantageous. On such a rotatable carrier means, the individual radiation sources can be arranged at a fixed radius to the carrier means' axis of rotation. For example, it is possible to arrange a plurality of, for example, 16 sources of radiation at a fixed or also a variable angular spacing on a circular arc segment. Many spectrally different sources of radiation increase the wavelength resolution.

The radiation sources are preferably arranged on the carrier means' retaining means such that an axis of the emitted light runs substantially parallel to the rotational axis of said carrier means. It is also possible for the angle between the illuminating axis and the rotational axis to be a specific one. A vertical alignment is also possible. The angle chosen is contingent upon the type of construction and other geometry.

Rotating of the carrier means allows the individual radiation sources to emit light successively to the aperture means. Each individual source of radiation can thus substantially be aligned to the aperture means so as to radiate a pre-definable or also as high of a radiation component as possible toward the aperture means. An increase in intensity is possible.

This enables the configuration to achieve a high degree of flexibility. In addition, an advantage is an increased reproducibility of the emitted radiation when using different illuminating devices of identical or differing constructions. Efforts spent making adjustments can be reduced while ensuring the corresponding reproducibility, respectively better overall results can be achieved.

The rotational range of the carrier means can be restricted to an angle of less than 360°; for example, rotational ranges of 270°, 300° or 330° are preferential. The individual sources of radiation will then be arranged at an angular spacing of roughly, for example, 5°, 10°, 15°, 20°, 30° or the like.

A positioning control means for specifying the position of the carrier means is preferably provided. This may be, for example, a limit switch device. Two limit switch devices for both rotational directions are likewise possible. The positioning control means can also be realized as a light barrier or a magnet or the like.

This type of positioning control means allows for reliably defining at least a start and an end point to an illumination series. Which thus largely excludes inaccuracies in positioning accumulating over longer operating periods.

In a preferred embodiment of the present invention according to one or all of the embodiments as previously described, a control sensor means is provided in the path of radiation, preferably arranged behind the aperture means. The control sensor means serves for the defining and control of the radiation emitted by each respective source of radiation. A control or regulation of the emitted output is also preferably possible.

With this type of control sensor means, the control means can control the motor device in dependent conjunction with the control sensor signal. For example, at a higher intensity of radiation, the motor device can operate faster and/or, at less intensity, can be controlled such that the carrier means moves slower or, at times, not even at all.

The inventive device for determining the visual properties of objects comprises at least a first optical means and at least a second optical means. The first optical means is configured as an illuminating means with which light can be emitted onto a measurement surface. At least the second optical means is configured as detector means with which the light reflected from the measurement surface or transmitted through the object can be measured. Hereby, the light reflected from the measurement surface or transmitted through the object is to be understood as that portion which is emitted by an illuminating means and reflected/transmitted by the measurement surface to ultimately reach the corresponding detector means.

The detector means can output at least one measurement value which is characteristic of at least a portion of the received light. The inventive device provides for a memory means for storing at least one and preferably a plurality of measurement values. At least one control means serves to control the measurement sequence.

At least one characteristic parameter characterizing the measurement surface is determinable with the device.

The first optical means configured as illuminating means comprises at least one aperture means and at least one scattering or diffusing means arranged in the path of radiation. Said at least one illuminating means comprises at least two sources of radiation, whereby the light emitted from at least two—preferably 3, 4 or more—sources of radiation is substantially directable to the aperture means.

As an example, two, three or more sources of radiation can be aligned substantially parallel to one another. At least a portion of the light emitted from two, three or more sources of radiation can be directed to a common point or light spot when both radiation sources are operated simultaneously. Preferably, at least a portion of the respectively emitted radiation is directed to a common area.

The inventive device has numerous advantages.

The inventive construction allows for increasing the reproducibility of measurements. The interoperability of different measuring devices is also improved.

Pursuant to the preferred embodiments, the inventive device comprises at least one illuminating means in accordance with the previously described claim 1 and its embodiments, so that the above description is also referred to with respect to preferred configurations.

In an embodiment of the present invention, at least the first and at least the second optical means are each arranged at a predefined azimuth angle and at a predefined angle of height to the measurement surface.

Arranging the individual optical means at selected angles with respect to the measurement surface ensues hereby preferably in accordance with the recognized national or international standards for the measuring of surfaces. Hereto, preferably the so-called 0°/45° geometry of illumination/detection is realized, as is standard when making color measurements.

Likewise preferred especially for the measurement of gloss and the like—but not limited solely thereto—is a symmetrical arrangement to the illuminating and detecting means, whereby angles of 5°, 20°, 30°, 45°, 60° and 85° to the measurement surface are preferred. Yet also angles of between 0° and 90° are moreover possible for the arrangement of the individual illuminating, detecting means respectively.

Particularly preferred are geometries which meet national and international standards. A configuration corresponding to the American ASTM E 430 norm or to the ISO 2813 or the DIN 67530 standard is preferential.

Having the sum of the optical means total at least three is especially preferred, while providing four, five or more optical means is particularly preferred. In so doing, each optical means can be configured as detector means or as illuminating means.

It is especially preferred to arrange a plurality of optical means across at least one range of angles—not just in one plane—but rather in the half-space above the measurement surface, so as to enable a three-dimensional measuring of the measurement surface.

For this reason it is preferred to dispose at least one third optical means outside of a first measurement plane extending through the first optical means, the second optical means, and the measurement surface.

Preferably the detector means comprises sensor means arranged in rows and/or columns. The detector means may be configured as a CCD chip. It is also possible for each individual sensor means to be configured to be color-sensitive by, for example, allocating at least three photo-sensitive elements of different spectral sensitivity to each respective sensor means. Sensor means configured in this manner then allow for the determining of color from the received light.

As an example, the detector means can be configured as a color CCD device. It is also likewise possible for the detector means to be configured as a spectrometer. Hereto, same can split impinging light into its various spectral components so as to attain a (highly resolved) spectrum. It is hereby also possible to spectrally split each individual localized portion of the received light in order to receive a localized spectral reading from the measurement surface. This can be realized by, for example, multiplexer optical fibers respectively registering areas of the measurement surface.

Preferably at least some of the sensor means are each allocated to different measuring points on the measurement surface respectively.

Acquiring the spectral characteristics of the measurement surface is also possible, especially in the case of the embodiment of the invention in which the individual radiation sources of an illuminating means emit radiation successively.

When a number of spectrally-differing sources of radiation emit radiation substantially successively onto the measurement surface, at least one measurement value can be registered by the detector means for the respective wavelength interval/emission spectrum. A consideration of the respective measurement values received with different sources of radiation allows for the deriving of a spectral progression for the measurement surface.

A plurality of 4, 8, 12, 16 or even more sources of radiation allows for a reliable spectral measurement reading to be attained. Given spectrally-differing sources of radiation, a CCD chip or a diode array without RGB channels can also be utilized. B/W sensors are more economical and yield a better signal-to-noise ratio. To improve measurement results, 100 values can be averaged.

Should a spectrometer be utilized in the detector means, some or all of the sources of radiation can also emit light simultaneously when determining the spectral characteristics of the measurement surface.

The successive switching of individual sources of radiation when making use of a spectrometer yields a comparison of the—known—emission spectrum and the measured detector spectrum, allowing conclusions to be drawn about the fluorescent properties, etc. An evaluation then becomes possible, as is described in German patent application DE 199 627 79 A1 with reference to FIGS. 5a and 5b.

In a preferred embodiment of the present invention, at least one first predefined threshold is provided in the memory means. During the measuring procedure, the control means allocates a measurement value of a sensor means to a first surface type should same exceed said threshold.

A second threshold can likewise be provided, allocated to a second surface type, so that, for example, a second measurement value falling short of said second threshold becomes allocated to the second surface type. Additional threshold values or surface types can readily be provided in exactly the same manner.

This enables the surface to be subdivided into various different surface types which is of particular advantage when dealing with, but not limited solely hereto, heterogeneously reflective surfaces or heterogeneous objects.

The present inventive device preferably determines at least one characteristic parameter of the measurement surface, such determination referring to a visual characteristic such as gloss, color, orange peel, haze, distinction of image (DOI) and the like. Being able to also determine several different characteristic parameters as well as being able to determine several similar visual parameters for different measurement geometries and/or surface types is also of preference.

Being able to derive at least one statistical parameter of the measurement surface is also preferred. For example, the determining of the distribution of brightness, properties and/or color to the surface to be measured. It is also possible to derive, for example, one characteristic value each for the distribution of brightness in the first surface type and in the second surface type. It is likewise possible to determine statistical parameters, for example color distribution, across different measuring geometries.

By having the control means or an external computer perform an evaluation, the course of a statistical or visual characteristic parameter across the measurement geometry or the different surface types can ensue. An external computer can be linked via direct cable or have a wireless connection. A connection via mobile telephone or the internet, etc., is also possible.

In an embodiment in which at least one illuminating means comprises at least one carrier means on which the at least two sources of radiation are arranged, it is preferable for a motor device to be able to move said carrier means configured preferably rotatable about a central axis of rotation.

The radiation emitted by the respective sources of radiation is then directable to the slot means by the moveability of the carrier means.

Preferably, especially in the case of a moveable carrier means, a first set of measurement values for at least some of the radiation sources can be recorded during the movement of the carrier means from a first position to a second position in a first direction of movement. For example, 200 values are recorded for each source of radiation, of which the middle 100 in each case will be evaluated.

At least a first characterizing mean value and/or at least a first characterizing deviation value can be derived from at least a part of the first set of measurement values. Upon exceeding or falling short of a characteristic mean and/or deviation value of a corresponding predefined or also selectable reference value or reference range, the control means triggers a signal. This can have the effect of, for example, the results from the current measurement being rejected.

A relatively higher characteristic deviation value is yielded when, for example, the device is tilted on the measurement surface during a measurement. There will then be, for example, a first number of measurement values of high quality and a second number of distorted measurement values. The deviation between the two ranges can be determined from the deviation value, which in this case might lie outside of its predefined tolerance range. Plausibility tests could thus be run, which increases the quality and the reproducibility of the measurement results.

It is furthermore possible for the carrier means to be moved from the second position back to the first position in a second step while a second set of measurement values are being taken.

This enables the deriving of at least one second characterizing mean value and/or at least one second characterizing deviation value. With a subsequent control on the second characteristic mean and/or deviation value, the measurement values of the current measurement can also be accepted or rejected as a whole.

It is possible to compare first and second characteristic deviation/mean values with one another in a further step in order to accept values from a measurement, for example only when the difference between the deviation and mean values is within a certain predetermined range.

Upon exceeding or falling short of one of said mean and/or deviation or comparison values, a signal can be issued by an output means preferably disposed in the device, so that the user is notified about the deviation.

For increasing measurement reproducibility, a positioning control means can be provided for determining the position of the carrier means, for example to assist in the setting of a pre-specified initial position prior to each measurement.

With the control sensor means as preferably provided, arranged preferably in the path of radiation behind the aperture means, the light radiated by an illuminating means can be controlled or even directed. The detector means and also the motor device of the carrier means can likewise be controlled subject to the signal of the control sensor means.

For example, when the carrier means first starts to move, the radiation emitted by one source of radiation is initially blocked and does not substantially strike or penetrate the aperture means. The radiation sources are then typically switched off.

Should a source of radiation on the carrier means then move towards the aperture means, a smaller component of the emitted radiation will first pass through the aperture means. Not until the carrier means has been moved far enough will the radiation passing through the iris reach its maximum. The intensity of illumination will basically remain at this level until the source of radiation has been moved far enough so that another now larger portion of the radiated light becomes blocked by the aperture means. Thus, a course of intensity which approximates a trapezoidal form is yielded over a radiation source's progression of movement over the iris. Values can be taken and stored continuously during the entire course of movement.

It is preferable for a series of measurement values to be recorded by the one or more detector means while the intensity of radiation remains at its upper maximum range. This can be realized, for example, by taking measurements during the whole movement across the iris and, based on the course of intensity, then drawing on the mean or also the maximum half (or the "trapezoidal roof") for the measurement.

A larger number of measurement values can contribute to greater measurement accuracy. Although the quality is also dependent upon the individual exposure times, so that given an overall predefined measurement cycle, optimizing the number of measurement values and exposure times can follow for each individual measurement.

The aperture means is preferably of elongated configuration and the particularly preferred configuration is that of circular arc segment form.

When none of the light emitted by the sources of illumination penetrates the aperture means during measurement, at least one blank signal will preferably be recorded. Upon determining and considering of said blank signal, arising due to penetrating ambient or also diffused light, and by the electrical noise of the sensors or the A/D converter, measurement results can as a whole be even further improved.

A connective means is provided in the preferred embodiments of the present inventive illuminating means and/or inventive device for linking the inventive means/device to an external computer or the like. Said connective means can hereby be configured so as to enable a conventional communication link via a cable or also a wireless connection. For example, a wireless connection can be realized via an infrared interface. Furthermore, a data connection to an external computer can be set up over a telephone or mobile telephone, etc.

Making use of an external computer, connected to the inventive device or means via a point-to-point connection or even over the internet, etc., allows for exchanging of data.

A direct point-to-point connection via telephone line (dialing up a remote server via telephone) offers security advantages. On the other hand, encoded data can also be transmitted over the internet.

In such fashion, measurement results from the detector means and/or control means can be forwarded to an external computer. It is likewise possible to transmit information from an external computer to the local inventive device or means. Same is then preferably stored in a memory of the control means. The control program can thus also be updated as to its control of exposure or measurement procedures.

It is likewise possible for a calibration or also a test program for the illuminating means or measuring device to be updated or started from the external computer.

A calibration or analysis program can be started automatically on the means/device via the external computer, the results of which can be evaluated locally or on the remote computer. New calibration values, for example, can be defined from the data as acquired; these can then be stored long-term in the device.

An alarm or notification signal can issue from the local device in the event of large or in some other way flagrant deviations. In order to prevent improper illuminations or distorted measurements, it is likewise possible for the local device to be taken out of operation in the event of serious shortcomings.

Further advantages and application possibilities will yield from the following description of embodiments.

Figure 2:
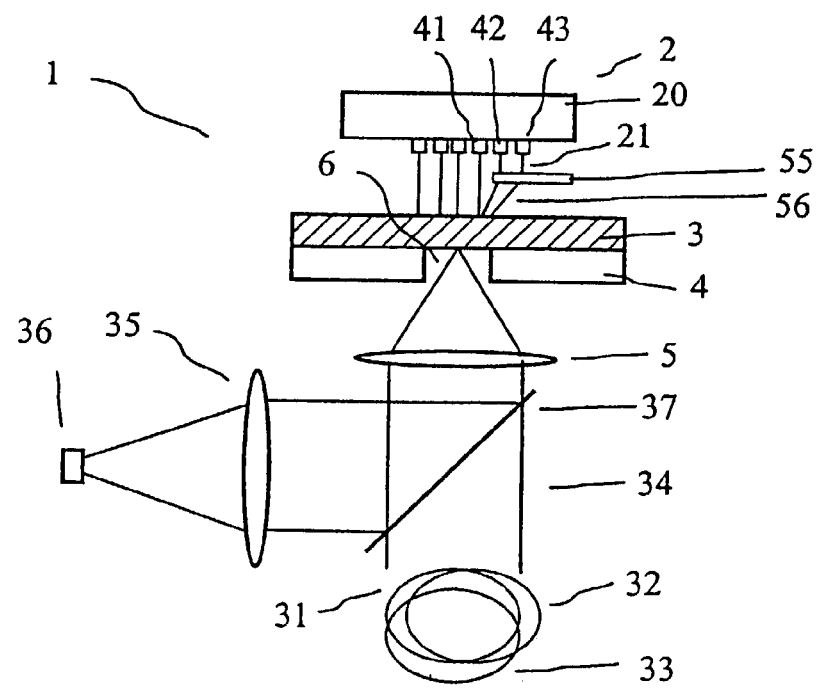
Figure 3:
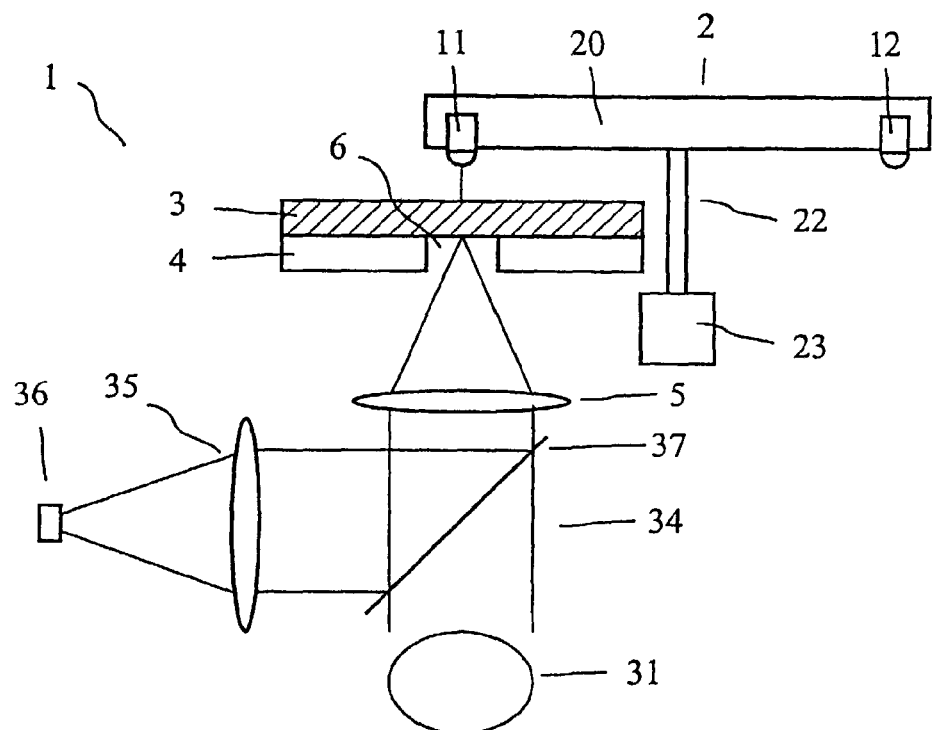
Figure 4:
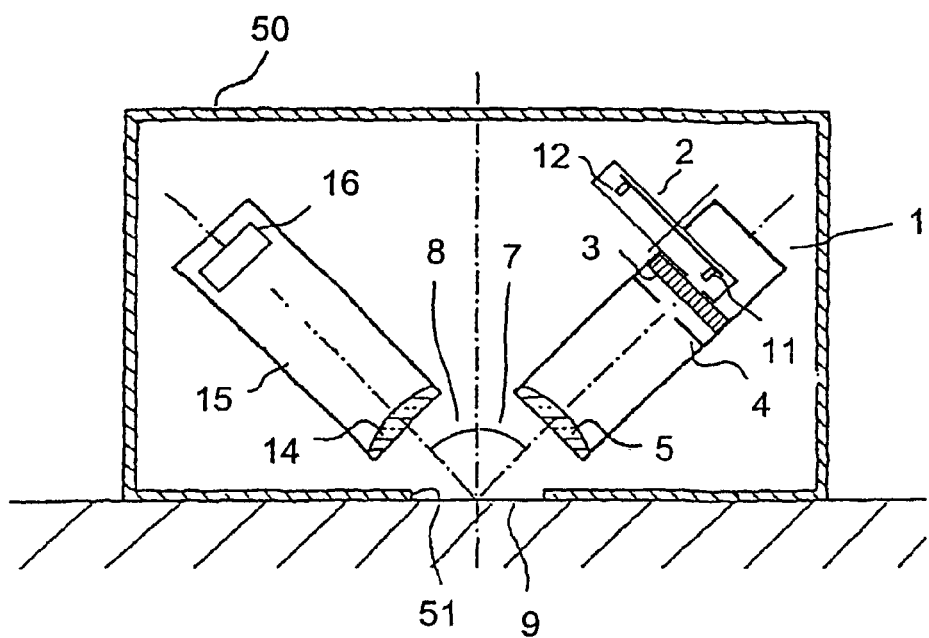
Figure 5:
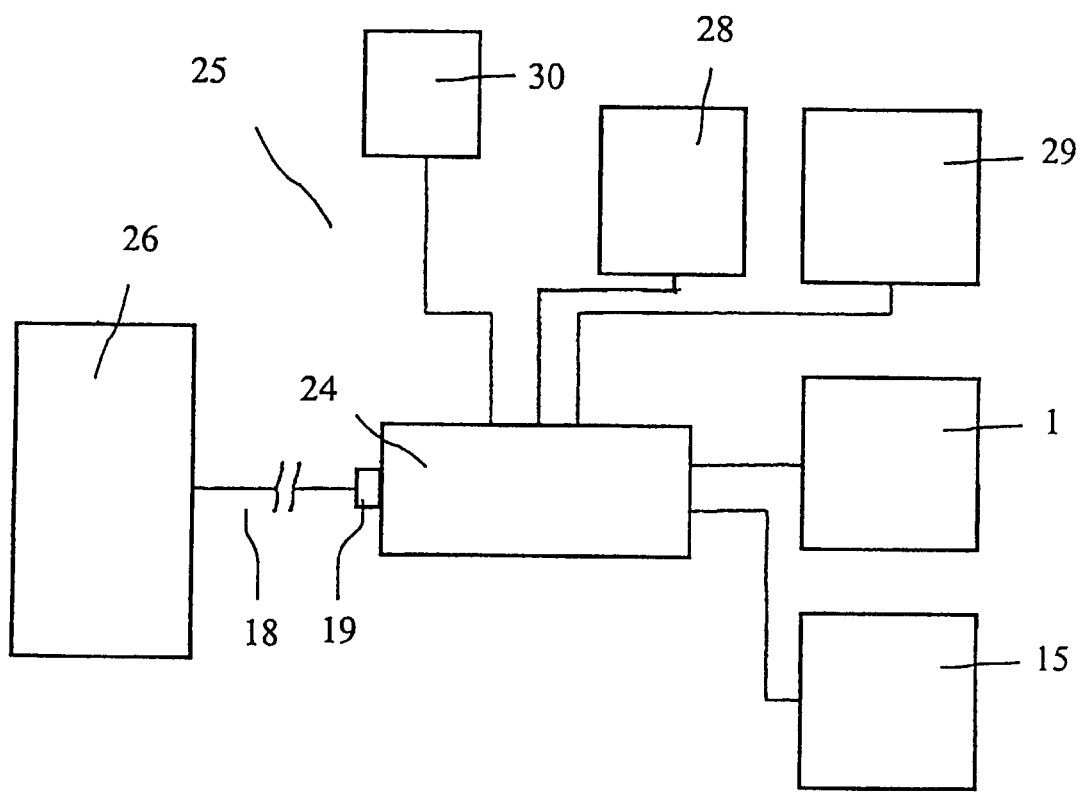
Figure 6:
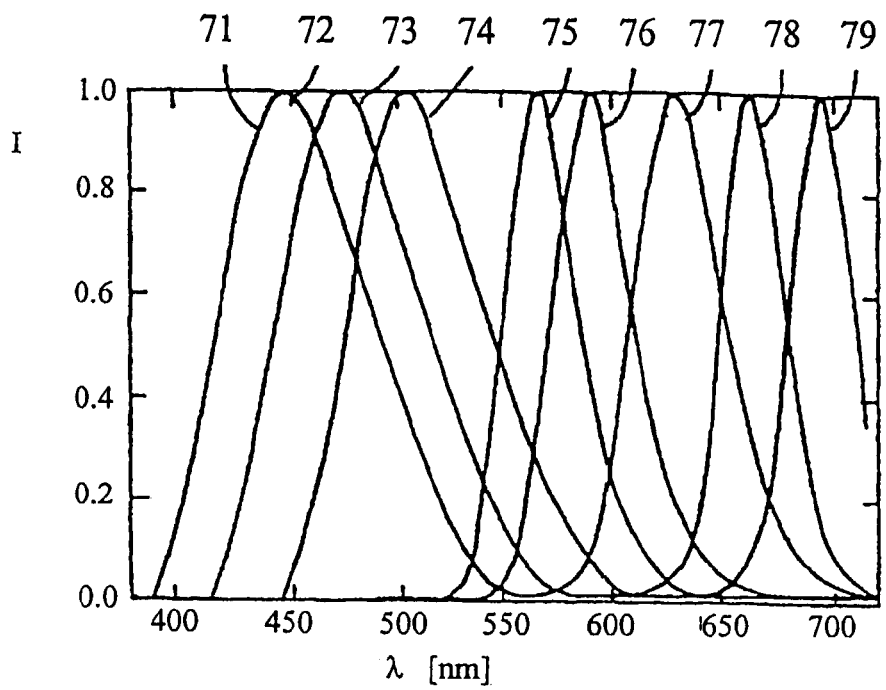
Figure 7:
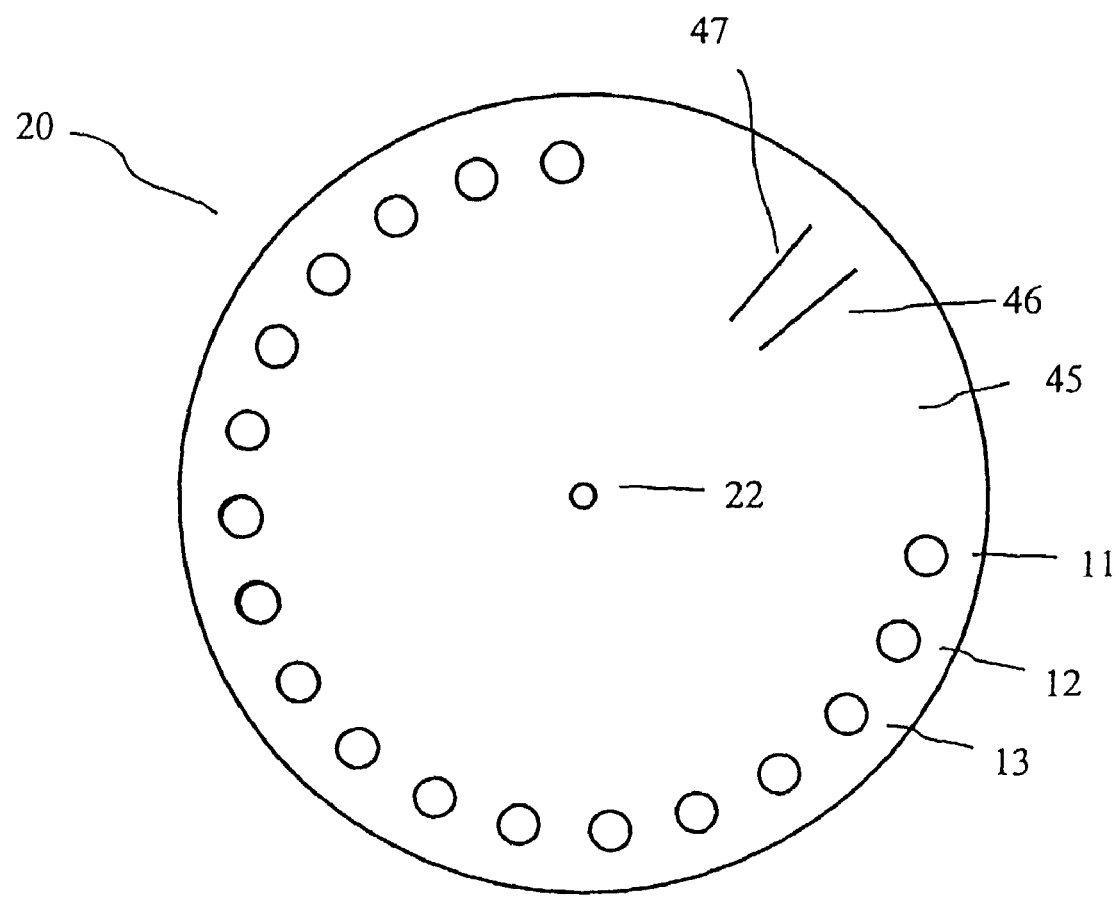
Figure 8:
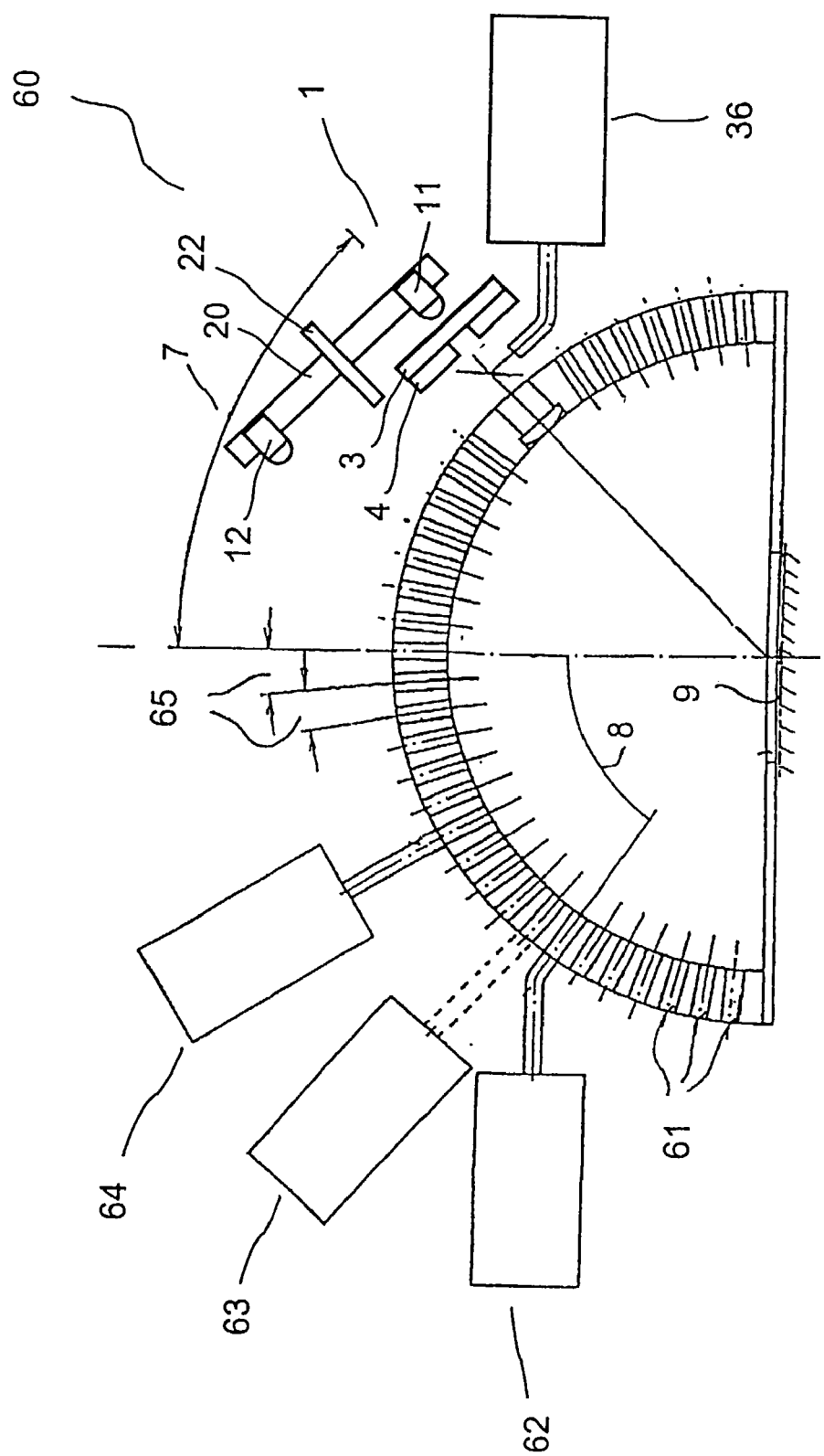

The drawings show:

FIG. 1 a first embodiment of an inventive illuminating means;

FIG. 2 a second embodiment of an inventive illuminating means;

FIG. 3 a third embodiment of an inventive device;

FIG. 4 a first embodiment of an inventive device;

FIG. 5 the principal technical circuitry configuration of the embodiment according to FIG. 4;

FIG. 6 emission spectra of nine selected light-emitting diodes corresponding to the embodiment according to FIGS. 1–4;

FIG. 7 a top plan view of a carrier means of the embodiment according to FIGS. 3 and 4;

FIG. 8 a second embodiment of the inventive device; and

Figure 9:
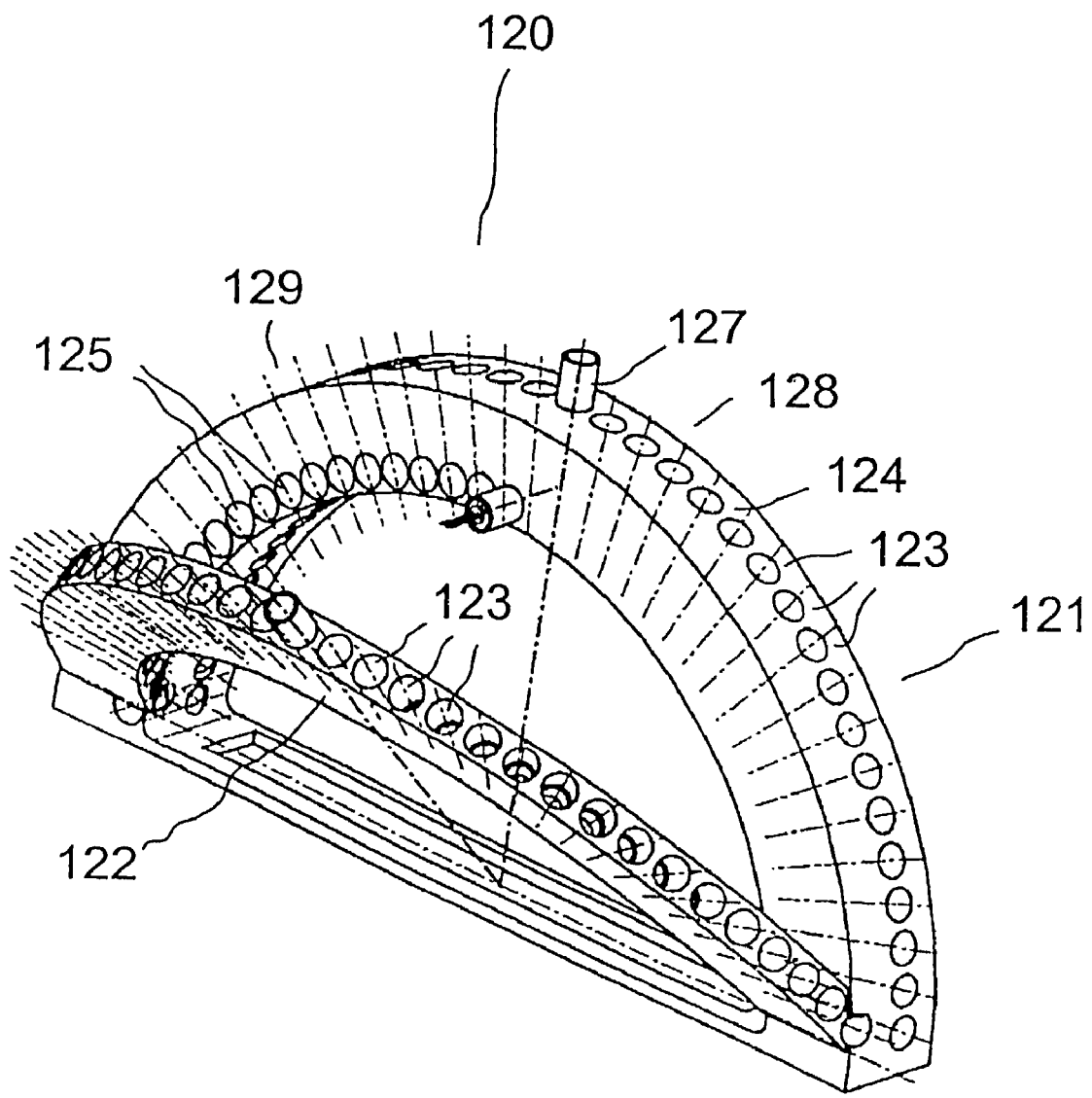

FIG. 9 a third embodiment of the inventive device.

A first embodiment of the present inventive means for the illuminating of a measurement surface will now be described in the following with reference to FIG. 1.

The illuminating device, the whole of which is specified by reference numeral 1, comprises an illuminating means 2 having a carrier 20 on which up to 16 or more different light-emitting diodes 11, 12, 13 are affixed. To enable a readily grasped overview, the representation according to FIG. 1 only shows five light-emitting diodes in the plane of intersection, although this representation of the embodiment according to FIG. 1 comprises additional light-emitting diodes which are not depicted and which are distributed spatially outside of the plane of intersection in front of and behind those light-emitting diodes as depicted.

Each light-emitting diode 11, 12, 13 is directed toward slot 6 in iris 4 for the purpose of attaining high intensity at the slot.

A scattering means or diffuser 3 is arranged in the path of radiation in front of iris 4, same serving for the homogenizing of the radiation passing through the slot.

A lens 5 is provided further along in the path of illumination for widening the beam of illumination 34. A beam splitter 37 decouples a smaller component thereof and diverts it through lens 35 to control photocell 36. Control photocell 36 regulates the intensity of the light 34 radiated to the measurement surface. A control means 25 (cf. FIG. 5) regulates the radiated intensity of the beam 34, respectively regulates same in conjunction with the signal of photo sensor 36.

Without diffuser 3, there would be considerable differences—even given uniform light-emitting diodes 11, 12, 13—in the illumination of the measurement surface since the individual light sources would direct beams of light (e.g. 21) at different angles onto slot 6 of iris 4. Without diffuser 3, different illuminated areas would correspondingly result on the measuring surface for each source of radiation.

By making use of diffuser 3, these type of influences are greatly diminished, whereby the extent of the effect is also dependent upon the scattering efficiency of diffuser 3. With typical transmissions in the range of between 0.05 and 5%—depending on particular application—utterly adequate homogeneous results are attained on the measurement surface, in which even areas 31, 32 and 33 of differing illumination can be detected contingent upon which light-emitting diode 11, 12 or 13 occasioned the illumination.

Since the areas are illuminated differently due to the differing directions of illumination emanating from light-emitting diodes 11, 12 and 13, etc., the light-emitting diodes are arranged as close as possible to one another so as to keep the angle to slot 6 of iris 4 small for the purpose of attaining a homogeneous illumination.

A further possibility is that of increasing the distance to the iris; although this measure is coupled with a decrease in light intensity. Optimizing intensity of illumination and homogeneity of the illuminated surface arises. A further possibility to effect an influence on the homogeneity involves the size of slot 6 of iris 4.

The same components of the inventive illuminating means depicted in the second embodiment according to FIG. 2 have been given the same reference numerals as in the embodiment according to FIG. 1, so that there is no need to go into a detailed discussion of these same components here.

In contrast to the embodiment in accordance with FIG. 1, semiconductor illuminating elements are provided in the embodiment according to FIG. 2 which are configured without a glass body to influence beam propagation. The individual sources of radiation 41, 42 and 43 are disposed directly on the die and affixed to a non-conductive part of carrier 20.

Since the individual components substantially have no housing—as would conventional light-emitting diodes—the packing density of the individual sources of radiation on substrate 20 can be increased considerably. With this type of configuration, many semiconductor radiation sources can be arranged on an area having a diameter of approx. 1 cm. For example, 16 or more semiconductor radiation sources are provided in the embodiment.

It is also possible for 8, 10, 12, 14, 16, 18, 20 or even more different sources of radiation 41, 42, 43 to be disposed on carrier 20.

Hence, in both the embodiment as according to FIG. 1 as well as in the other embodiments, the individual sources of radiation exhibit different spectral emission characteristics, whereby the individual spectra overlap at least sectionally and, taken as a whole, substantially cover the entire visual range of the spectrum.

The control means of the illuminating means allows for the individual light-emitting diodes 11, 12 and 13 in FIG. 1 or the semiconductor radiation sources 41, 42 and 43 in FIG. 2 to radiate light onto the measurement surface to be analyzed both simultaneously as well as also successively. With a successive illumination, individual temporally illuminated sections can also overlap so that at times two or even more sources of radiation may emit light simultaneously onto the surface to be analyzed.

A light guiding means 55 is provided in the embodiment according to FIG. 2 which may, however, also be utilized in other embodiments.

Said light guiding means may be configured as a conventional lens acting on all light radiating elements or also only on some of the light radiating elements, as is depicted in FIG. 2 with radiating elements 42 and 43.

Light guiding means 55 is configured in the embodiment as a conventional lens or lens segment which conveys incident light of radiating elements 42 and 43 centrally to slot 6 of iris 4. The beam of light 21 radiated by radiating element 43 is focused as beam 56 onto the slot by light guiding means 55.

It is also possible to utilize light guiding means 55 in a manner of using holographic-optical elements and/or microlenses in order to divert light from individual radiating elements in precise fashion.

In contrast to the embodiment in accordance with FIG. 1, by using non-optic semiconductor emitters in the embodiment according to FIG. 2, the light emitted directly by the individual radiating elements is normally of less directional strength, yet has a preferred direction perpendicular to the exit surface (indicated in FIG. 2 by beam direction 21 for radiating element 43).

The lower intensity which thus ensues can conceivably be compensated for by a higher packing density and a lower distance from the slot, particularly—however not only when—light guiding elements 55 are utilized.

Due to the smaller dimensions of the individual radiating elements, they can be packed closer together so that a greater number of radiating elements can be fit on the same surface.

An arrangement according to FIG. 2 likewise allows for the attaining of a considerable homogenization to the radiation on the measurement surface from different sources. A diffuser 3 is likewise provided as in the embodiment according to FIG. 1.

It can, however, be ascertained even with an arrangement according to FIG. 2 that in the case of highly-sensitive measuring devices, there is a dependency between the illuminated area on the object to be analyzed and the light-emitting element. As in the embodiment according to FIG. 1, an optimization can follow here based on the geometry of the arrangement and the scattering effect of the diffuser.

In the embodiment according to FIG. 3, the same components as in the preceding embodiments have again been given the same reference numerals.

In the embodiment according to FIG. 3, radiating means 2 of illuminating means 1 is configured to be rotatable. A total of 16 different light-emitting diodes are arranged across a 270° angular range on carrier disk 20, coupled rotatably to stepper motor 23 about central axis 22. All the light-emitting diodes are preferably positioned at a constant radial distance from the axis of rotation. Upon turning of carrier disk 20, all 16 of the light-emitting diodes 11, 12 given in the embodiment can be centrally positioned above slot 6 of iris 4. Iris 4 measures approximately 1×3 mm.

An illuminated area 31 on the surface to be measured is thus yielded for each of the light-emitting diodes 11, 12 at suitable angular position. The light pattern resulting from of the various light-emitting diodes hereby differs substantially only in intensity and illumination spectrum, but not in form.

When illuminating a surface to be measured, each individual light-emitting diode 11, 12, etc. can be brought into position successively by the stepper motor 23 of illuminating means 2, so that upon a rotation of a maximum of 360°, each of the light-emitting diodes can emit radiation onto the surface to be analyzed.

Since each light-emitting diode 11, 12 is aligned by a simple turning of carrier plate 20 in relation to slot 6 of iris 4 for measuring, diffuser 3 can, in contrast to the preceding embodiments, exhibit a considerably higher transmission—with the same or a higher quality of illumination—since the diffuser does not have to homogenize the different illuminating means to such a strong degree. Transmission values as yielded by this embodiment are greater from those in the preceding embodiments by a factor of about 10 or even more, while the homogeneity to the illumination of the light spot on the surface to be measured even increases.

While a diffuser as utilized in typical cases of application when assessing surfaces in the automobile sector has, for example, a transmission of 0.2% in the embodiments according to FIGS. 1 and 2, the transmission can be increased to about 2% in the embodiment according to FIG. 3. This yields a substantially higher illumination intensity, by a factor of 5 up to a factor of about 15, which leads to a better signal-to-noise ratio and also a better quality to the measurement results.

Another advantage is the increased interoperability of different illuminating devices. Among other factors, this has to do with the effort required in adjusting the light-emitting diodes being less in the embodiment according to FIG. 3 than in the preceding embodiments so that any typical deviation is lower: the light sources radiate to the slot contingent upon the system.

Light-emitting diodes can be mounted on carrier wheel 20 of the illuminating means according to FIG. 3 in such a manner that their optical axes are at an angle to the axis of rotation. As an example, the light-emitting diodes can also be disposed on the outer circumference of the carrier plate and outwardly emit radiation tangentially or radially or the like. Hereto, the carrier means' axis of rotation should be aligned vertically to the optical axis of the radiation sources.

However, also feasible is a conical arrangement in which the light-emitting diodes emit light at an angle of e.g. 45° to the carrier means' axis of rotation.

FIG. 4 represents an inventive device 50 which is configured here as a device for measuring gloss.

Gloss-measuring device 50 comprises a housing in which a housing opening 51 is arranged at its base. An illuminating unit 1 is provided for emitting light onto measurement surface 9 at angle 7. The light reflected by the measurement surface at an angular range of angle 8, which in the embodiment amounts to 45° as does angle 7, is received by a detector unit 15. A lens 14 is arranged in detector tubus 15 which concentrates the light received from the surface onto photo sensor 16 which, in the embodiment, is configured as a two-dimensional CCD chip.

The embodiment provides for a monochromatic sensor; a color CCD chip or the like may however also be utilized.

Illuminating unit 1 comprises an illuminating means 2 which in the embodiment according to FIG. 4 is configured substantially the same as the illuminating means from the embodiment according to FIG. 3. The same components have again been given the same reference numerals.

Illuminating unit 1 comprises a rotatable light-emitting diode carrier disk on which light-emitting diodes 11, 12, etc. are arranged.

Rotatable carrier disk 20 is depicted in FIG. 7. Housings for 16 light-emitting diodes are provided in carrier disk 20. The light-emitting diodes are arranged circularly around the central axis of rotation 22 of carrier disk 20 and exhibit an angular displacement of 15° to one another. This thus yields an angular range of about 240° for 16 and 270° for 18 light-emitting diodes while no light-emitting diodes are arranged across an angular range of about 90°.

Two limit switches 46, 47 are provided in this area which are triggered upon the reaching of a limiting signal. The limit switches can be of conventional configuration such as mechanical switches, although optical light barriers or the like may also be utilized. It is likewise possible for only one limit switch to be provided for both directions of rotation.

Limit switches 46, 47 allow for a calibration of zero when starting each measurement or at selected or selectable intervals of measurement or time.

To perform measurements, carrier disk 20 of illuminating means 2 is rotated, for example, until light-emitting diode 11 is aligned along the optical axis. The light emitted by light-emitting diode 11 strikes diffuser 3 and is (related to the local distribution) homogenized by the diffuser having, as in the previous embodiment, a transmission of roughly 2%. The light exiting slot 6 of iris 4 is parallelized by lens 5 and strikes measurement surface 9. In other embodiments, lens 5 can also serve to focus onto the measurement surface.

While light-emitting diode 11 emits light, detector 16 receives a portion of the reflected light and the measurement result is stored to memory 28 of control means 25. Control means 25 has a processor unit 24 which controls the measurement sequence based on a program stored in memory 28. User interaction is possible via input 29 with output in the form of a display 30 on the device.

Interface 19 serves for the connection to an external computer 26 via data line 18. The data link may also ensue in wireless fashion and/or over the internet. An automatic or interactive test or a calibrating of the device can ensue via connective link with, e.g., the manufacturer of the device, whereby the corresponding test and calibration results or corrected values can then also be preferably saved to the device. Transmitting of measurement data to an external or central mainframe computer during production is likewise possible, so that even while measurements are still being made, the operational production can already be evaluating and taking the measurement results into account.

Besides for the indicated geometry, 45° illumination and 45° detection, a geometry of particularly 0°, i.e., perpendicular to the surface for illumination and 45° for detection and vice-versa is also possible. The 0°/45° geometry is used as a standard especially in color measuring. With the inventive illuminating means, many sources of radiation of differing wavelength can be drawn upon to carry out exact color measurings utilizing a monochromatic sensor. The formulas and mathematical guidelines utilized hereto have already been described in German patent application DE 4 434 168 A1, the content of which, especially pages 1–12, also being herewith made an object of the present application.

Moreover, the device depicted in FIG. 4 may also comprise a detector means or illuminating means which is aligned at 5°, 20°, 30°, 60° or 85° to the measurement surface.

A measurement cycle lasts about 0.5 to 5 seconds (3 seconds is typical). In measuring, the peak for each respective source of radiation can also be sought out by rotation. A series of values can then be taken at standstill for a subsequent evaluation.

In FIG. 6, nine spectral emission characteristics of different light-emitting diodes 11, 12, etc. are depicted as an example. The embodiment makes use of 16 light-emitting diodes having different spectral emission dynamics. It is however also possible to use a lesser or greater number of different light-emitting diodes or semiconductor sources of radiation.

FIG. 8 depicts a further embodiment of inventive measuring device 60. Illuminating unit 1 is configured in correspondence to the embodiment according to FIG. 3. The carrier disk for light-emitting diode 20 is mounted rotatable about axis of rotation 22.

Light-emitting diodes 11, 12, etc. are arranged on the carrier disk, same being movable upon rotation in the optical axis. The light emitted by light-emitting diode 11 (in the position as per FIG. 8) strikes diffuser 3.

A portion of the light passing through slot 6 of iris 4 is registered by control sensor 36. Control sensor 36 in the present embodiment is configured as a small spectrometer and controls the emitted spectrum. The light radiated onto measurement surface 9 is reflected at different steradian angles. Detector means 62, 63, 64 are provided at different angles to receive the light reflected from the respective directions.

Detectors 62, 63 are likewise configured as spectrometer in the present embodiment, fed light via optical fibers. The device 60 comprises retaining means 61 disposed at angular spacing 65 in a semicircle perpendicularly above the measure-ment surface. In the selected example, the angular spacing 65 to the retaining means amounts to 5°. Meaning detection of the reflected light ensues at 5° spacings. It is likewise possible to make use of more than three detectors, whereby individual detectors can also be moved from one position to another.

It is furthermore pointed out that, just as in the embodiment according to FIG. 4, an illuminating means pursuant to FIG. 1 or FIG. 2 may also be utilized in the embodiment according to FIG. 8.

A further embodiment will now be described with respect to FIG. 9.

The measuring device 120 depicted in perspective in FIG. 9 comprises a first subframe, measuring circle 121 respectively, extending in semicircular fashion above measurement surface 9. A plurality of retaining means in the form of bore holes 123 is provided within measuring circle 120.

At least one of the illuminating means from FIGS. 1–3 is provided to radiate light through one of the openings 123 onto measurement surface 9.

Detector units or optical fibers may be inserted into other bore holes 123 which then conduct the respectively received light to a sensor.

Should detector units be inserted into bore holes 123, same can be provided with a two-dimensional CCD sensor for the purpose of recording a two-dimensional image of the surface.

The angular spacing from one bore hole 123 to the next bore hole 123 is firmly set in the embodiment as depicted and amounts to 5°. Although it is to be pointed out that other angular spacings such as 2.5° or 3° or 10° or the like are also possible. It is also conceivable that bore holes not be provided across the semicircle's entire angular range of 180°, but rather only at one or more angular ranges.

The inventive device 120 moreover comprises a second measuring circle 122 which in the embodiment is arranged at 45° to a plane through the first measuring circle and to the measuring plane. Yet this angle may also have another value and especially that of 10°, 15°, 20°, 25°, 30°, 60° or 75°. The light radiated by the illuminating means can be received by a plurality of detector means, same being distributed in the half-space above the measurement surface. This allows for three-dimensional measuring of the visual properties of an object to be measured, which is of particular advantage with respect to structured surfaces. Three-dimensional measuring is also advantageous as regards objects having material inclusions such as flakes and the like. Taking measurements across a plurality of angles enables a statistical evaluation of color impression, gloss, etc.

Should measurements of locational resolution be conducted, the values for the differing surface types can be determined separately so that, for example, one characteristic parameter for a color of a material inclusion and one characteristic parameter for the color of the rest of the surface without material inclusions will be determined.

For the further configuration and conducting of measurements on heterogeneously reflective objects with an inventive device, reference is made to the contents of the applicant's German patent application bearing the file number 10122917, whereby in particular the contents of description pages 1–55 as well as FIGS. 1–12 are herewith also made an object of the present patent application.

What is claim is:

1. An illuminating means for illuminating a measurement surface comprising:
    at least one radiating means having at least two sources of radiation, wherein said at least two sources of radiation are arranged on a movable common carrier means;
    at least one aperture means;
    at least one scattering means arranged in the path of radiation;
    wherein the radiation emitted by the sources of radiation is directable to said aperture means; and
    wherein at least two sources of radiation exhibit different spectral characteristics.

2. The illuminating means according to claim 1, wherein the number of radiation sources of said radiating means is taken from a group of numbers which includes the reference numbers 3, 4, 5, 6, 7, 8, 9, 10, 11, 12, 13, 14, 15, 16, 17, 18, 19, 20, 24 and 28.

3. The illuminating means according to claim 1, wherein at least one of the at least one radiating means emits radiation across the entire visible range of the spectrum.

4. The illuminating means according to claim 1, wherein at least one source of radiation is taken from among a group of radiation sources which includes thermal sources of radiation, semiconductor sources of radiation, and light-emitting diode devices.

5. The illuminating means according to claim 1, wherein a control means is provided.

6. The illuminating means according to claim 5, wherein the radiating means is controllable by said control means such that at least two sources of radiation emit radiation successively over a period of time.

7. The illuminating means according to claim 5, wherein the radiating means is controllable by said control means such that at least two sources of radiation emit radiation substantially simultaneously.

8. The illuminating means according to claim 1, wherein at least one light guiding means is provided in the path of radiation between at least one source of radiation and the aperture means.

9. The illuminating means according to claim 8, wherein at least one light guiding means comprises at least one light guiding element taken from among a group of light guiding elements which includes lens elements, micro-lens elements, micro-lens arrays, diffraction elements, grid elements, volume grid elements, and holographic optical elements.

10. The illuminating means according to claim 1, wherein said sources of radiation are arranged on said carrier means such that the radiation as emitted is directed to said aperture means.

11. The illuminating means according to claim 1, wherein said sources of radiation are configured as silicon chips and arranged adjacent one another on said carrier means.

12. The illuminating means according to claim 1, wherein said sources of radiation are arranged on said carrier means such that the respectively emitted radiation is directable to the aperture means in solely substantially individual fashion.

13. The illuminating means according to claim 1, wherein a motor device is provided for a controllable movement of said carrier means which is taken from a group of motor devices which includes electric motor devices and stepper motor devices or other similar devices.

14. The illuminating means according to claim 1, wherein said carrier means is rotatable through at least one angular range.

15. The illuminating means according to claim 1, wherein sliding contact means are provided on said carrier means for transmitting electrical power to said sources of radiation.

16. The illuminating means according to claim 1, wherein a positioning control means for specifying the position of the carrier means is provided.

17. The illuminating means according to claim 1, wherein a control sensor means is provided which receives a portion of the radiation as emitted and issues at least one control sensor signal.

18. The illuminating means according to claim 17, wherein said control sensor means is arranged in the path of radiation behind the aperture means.

19. The illuminating means according to claim 17, wherein said control means controls a motor device in dependent conjunction with said control sensor signal.

20. A device for determining the properties of reflective objects comprising:

at least one first optical means configured as an illuminating means and with which light is emittable onto a measurement surface;

wherein at least said first optical means comprises at least one aperture means and at least one scattering means arranged in the path of radiation;

wherein said first optical means includes at least one radiating means having at least two sources of radiation;

wherein the radiation emitted by said at least two sources of radiation is directable to said aperture means;

at least one second optical means configured as detector means and with which the light reflected from the measurement surface is measurable;

wherein at least one measurement value which is characteristic of at least a portion of the received light is outputable by said detector means;

at least one memory means;

at least one control means for controlling the measurement sequence;

wherein at least one characteristic parameter which characterizes the measurement surface is determinable; and wherein said at least one characteristic parameter is taken from among a group of parameters which includes visual characteristics, such as gloss, color, orange peel, haze, distinction of image and other similar properties and including statistical parameters, such as distribution of brightness, size and color.

21. The device according to claim 20, wherein at least said first and at least said second optical means are each arranged at a predefined azimuth angle and each substantially at a predefined angle of height to said measurement surface respectively.

22. The device according to claim 20, wherein the sum of the number of detector means and the number of illuminating means amounts to three, four, five, or more.

23. The device according to claim 21, wherein at least one third optical means is arranged outside of a first measurement plane which extends through said first optical means, said second detector optical means, and said measurement surface.

24. The device according to claim 20, wherein at least one of said at least one detector means comprises sensor means arranged in rows and columns.

25. The device according to claim 24, wherein at least some of said sensor means are each allocated to different measuring points on said measurement surface respectively.

26. The device according to claim 20, wherein at least one detector means comprises multiple sensor means having different spectral sensitivities.

27. The device according to claim 20, wherein at least one detector means comprises at least one spectrometer means so that a spectral characteristic of the received light is ascertainable.

28. The device according to claim 26, wherein said control means evaluates the spectral sensor signals and determines fluorescence effects for the surface to be measured taking the spectral properties of the radiating means into account.

29. The device according to claim 20, wherein at least one first predefined threshold is provided in said memory means;

wherein a measurement procedure is controllable by said control means such that a measurement value of one sensor means is allocated to a first surface type, should same exceed said first threshold.

30. The device according to claim 20, wherein at least two or more different characteristic parameters are determinable for said measurement surface.

31. The device according to claim 20, wherein at least one characteristic parameter is determinable respectively for at least two or more different measurement geometries, wherein each measurement geometry is characteristic for the respective angle of illumination and the respective angle of measurement.

32. The device according to claim 31, wherein a statistical distribution of at least one statistical characteristic parameter and visual characteristic parameter of at least one surface type is derivable across a plurality of at least two measuring geometries.

33. The device according to claim 20, wherein said first optical means comprises a carrier means on which at least two sources of radiation are arranged.

34. The device according to claim 33, wherein said carrier means is movable by a motor means.

35. The device according to claim 33, wherein the radiation emitted by at least two sources of radiation is only directable to the aperture means in substantially successive fashion due to the movement of the carrier means.

36. The device according to claim 33, wherein said carrier means is rotatable through at least one angular range,
wherein the sources of radiation are preferably arranged in a circle at predefined angular spacings around an axis of rotation.

37. The device according to claim 36, wherein said control means can control a measurement sequence such that a first set of measurement values for at least some of the radiation sources is recordable upon a rotation of the carrier means from a first position into a second position in a first direction of rotation.

38. The device according to claim 37, wherein at least one first characterizing mean value and at least one first characterizing deviation value is derived from at least the first set of measurement values, wherein a first characterizing deviation value greater than a predefined deviation value triggers a warning signal.

39. The device according to claim 37, wherein a measurement sequence is controllable by said control means such that a second set of measurement values is recorded for at least the same individual sources of radiation upon a rotation of the carrier means from the second back to the first position in the reversed direction of rotation.

40. The device according to claim 39, wherein at least one second characterizing mean value and at least one second characterizing deviation value is derived for the second set of measurement values, wherein a second characterizing deviation value greater than a predefined value triggers a warning signal.

41. The device according to claim 40, wherein a difference between said first and said second characterizing mean value greater than a predefined difference value triggers a warning signal.

42. The device according to claim 20, wherein a positioning control means is provided for determining the position of the carrier means.

43. The device according to claim 20, wherein a control sensor means is provided which receives a portion of the radiation as emitted and outputs at least one control sensor signal, wherein said control sensor means is preferably arranged in the path of radiation behind said aperture means.

44. The device according to claim 43, wherein said control means controls a motor device in dependent conjunction with said control sensor signal.

45. The device according to claim 43, wherein said control means controls an exposure time for said detector means in dependent conjunction with said control sensor signal.

46. The device according to claim 34, wherein said control means controls said detector means during movement over the aperture means such that a predetermined number of measurement values are taken.

47. A method for determining the properties of reflective objects utilizing a device comprising:
at least one first optical means configured as an illuminating means and with which light can be radiated onto a measurement surface;
wherein at least said first optical means comprises at least one aperture means and at least one scattering means arranged in the path of radiation, and wherein at least said first optical means comprises at least one radiating means having at least two sources of radiation, wherein the radiation emitted by said at least two sources of radiation is directable to said aperture means;
at least one second optical means configured as detector means;
at least one memory means;
at least one control means for controlling the measurement sequence;
wherein light from at least one source of radiation is directed to the aperture means and radiated onto the measurement surface;
wherein said detector means records at least a portion of the light reflected from the measurement surface and outputs at least one measurement value which is characteristic for at least a portion of said received light;
wherein said control means determines at least one characteristic parameter which characterizes at least one portion of the measurement surface based on a command sequence stored in the memory means; and
wherein said at least one characteristic parameter is taken from among a group of parameters which includes visual characteristics, such as gloss, color, orange peel, haze, distinction of image and other similar properties and including statistical parameters, such as distribution of brightness, size and color.

* * * * *